(12) United States Patent
Inui et al.

(10) Patent No.: US 12,376,614 B2
(45) Date of Patent: Aug. 5, 2025

(54) METHOD FOR PRODUCING HOP PROCESSED PRODUCT

(71) Applicant: SUNTORY HOLDINGS LIMITED, Osaka (JP)

(72) Inventors: Takako Inui, Ibaraki (JP); Hiroo Matsui, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 176 days.

(21) Appl. No.: 17/878,314

(22) Filed: Aug. 1, 2022

(65) Prior Publication Data
US 2022/0378074 A1   Dec. 1, 2022

Related U.S. Application Data

(62) Division of application No. 16/099,860, filed as application No. PCT/JP2016/064333 on May 13, 2016, now abandoned.

(51) Int. Cl.
| | |
|---|---|
| *A23L 33/105* | (2016.01) |
| *A61K 36/185* | (2006.01) |
| *A61K 36/85* | (2006.01) |
| *A61P 3/06* | (2006.01) |
| *A61P 39/06* | (2006.01) |
| *C12C 3/00* | (2006.01) |

(52) U.S. Cl.
CPC .......... *A23L 33/105* (2016.08); *A61K 36/185* (2013.01); *A61K 36/85* (2013.01); *A61P 3/06* (2018.01); *A61P 39/06* (2018.01); *C12C 3/00* (2013.01); *A23V 2002/00* (2013.01)

(58) Field of Classification Search
CPC ..... A23L 33/105; A61K 36/185; A61K 36/85; A61P 3/06; A61P 39/06; C12C 3/00; A23V 2002/00
See application file for complete search history.

(56) References Cited

U.S. PATENT DOCUMENTS

| | | | | |
|---|---|---|---|---|
| 5,798,150 A | * | 8/1998 | Morford | A01N 3/00 428/17 |
| 5,985,063 A | * | 11/1999 | Morford | A01N 3/00 428/17 |
| 8,349,375 B2 | * | 1/2013 | Kuhrts | A61K 36/185 424/725 |
| 2006/0233902 A1 | | 10/2006 | Yajima et al. | |
| 2007/0248549 A1 | * | 10/2007 | Kuhrts | A61P 1/02 424/778 |
| 2008/0008776 A1 | | 1/2008 | Back et al. | |
| 2008/0166303 A1 | * | 7/2008 | Tamarkin | A61K 8/046 424/43 |
| 2011/0280968 A1 | | 11/2011 | Back et al. | |
| 2012/0270950 A1 | | 10/2012 | Taniguchi et al. | |
| 2013/0316023 A1 | | 11/2013 | Manabe et al. | |
| 2014/0220179 A1 | | 8/2014 | Matsui et al. | |
| 2016/0053210 A1 | | 2/2016 | Nakahama et al. | |
| 2021/0076740 A1 | * | 3/2021 | Ouyang | A24F 40/40 |
| 2023/0372426 A1 | * | 11/2023 | Park | A61K 36/752 |

FOREIGN PATENT DOCUMENTS

| | | |
|---|---|---|
| CN | 102220194 A | 10/2011 |
| JP | 2004-81113 A | 3/2004 |
| JP | 2008-69072 A | 3/2008 |
| JP | 2008-174458 A | 7/2008 |
| JP | 2014-187969 A | 10/2014 |
| JP | 5599126 B2 | 10/2014 |
| JP | 2015-134771 A | 7/2015 |
| JP | 2015-224194 A | 12/2015 |
| WO | 03/068205 A1 | 8/2003 |
| WO | 2010/143719 A1 | 12/2010 |
| WO | 2012/081675 A1 | 5/2014 |

OTHER PUBLICATIONS

Sharp, D. C. et al., "Effect of Harvest Maturity on the Chemical Composition of Cascade and Willamette Hops", Journal of the American Society of Brewing Chemists, Dec. 12, 2014, vol. 72, No. 4, pp. 231-238; cited in ISR dated Aug. 16, 2016.
International Search Report dated Aug. 16, 2016, issued in counterpart International Application No. PCT/JP2016/064333. (2 pages).

(Continued)

*Primary Examiner* — Aaron J Kosar
*Assistant Examiner* — Jennifer Lynn Cain
(74) *Attorney, Agent, or Firm* — WHDA, LLP

(57) ABSTRACT

There is a method for producing a hop processed product. The hop processed product is for use in foodstuff for anti-adipocyte differentiation or for antioxidation. It contains 50% by weight or more, preferably 60% by weight or more, and more preferably 70% by weight or more, of hop flowers (E•M) showing hues satisfying that a value of a* is less than −0.5 in accordance with a CIE Lab color space, and preferably that a value of h is 90° or more in accordance with a CIE Lch color space. The hop processed product of the present invention has excellent action of anti-adipocyte differentiation or antioxidant action, so that the hop processed product can be expected to have effects in, for example, "anti-metabolic syndrome," "anti-aging," "anti-obesity," and the like.

8 Claims, 4 Drawing Sheets

(56) References Cited

OTHER PUBLICATIONS

Supplementary European Search Report dated Oct. 10, 2019, issued in corresponding European Patent Application No. 16901707.6-1106/3456207 PCT/JP20160164333 (13 pages).
Namikoshi, Tamehachi et al., "Isohumulones Derived from Hops Ameliorate Renal Injury via an Anti-Oxidative Effect in Dahl Salt-Sensitive Rats", Hypertens Res vol. 30, No. 2 (2007), pp. 175-184.
Tagashira, Motoyuki et al., "Antioxidative Activity of Hop Bitter Acids and Their Analogues", Biosei, Biotech, Biochem., 59 (4), pp. 740-742, 1995.
"Alpha acid", Wikipedia, (2 pages).

* cited by examiner

METHOD FOR PRODUCING HOP PROCESSED PRODUCT

CROSS-REFERENCE TO RELATED APPLICATIONS

This application is a divisional of U.S. application Ser. No. 16/099,860, filed on Nov. 8, 2018, which is a 371 of International Application No. PCT/2016/064333, filed on May 13, 2016, the entire contents of which are incorporated herein by reference.

TECHNICAL FIELD

The present invention relates to a hop processed product. More specifically, the present invention relates to a processed product usable as raw materials for foodstuff, a method for producing the hop processed product, foodstuff in which the hop processed product is used as raw materials.

BACKGROUND ART

Hops contain a variety of ingredients. For example, bitterness is attributable to an α-acid, hoppy aroma attributable to terpenes, and a body attributable to polyphenols, so that flavors are given by various ingredients, thereby making it possible to adjust the quality of a beer-taste beverage. On the other hand, these ingredients have been known to have various physiologically active actions, so that a hop or an extract thereof may be added to foodstuff with expectation of the functions in many cases.

For example, Patent Publication 1 discloses that a food blended with a humulone, which is an ingredient in a hop, or an isohumulone, which is contained in an isomerized hop extract, has an effect of increasing the dopamine production, thereby ameliorating or improving cognition functions.

In addition, an alkali-degradation product in which a hop extract is degraded under alkali conditions or a hop oxidation reaction product obtained by contacting a hop with oxygen in the air to oxidize has an action of anti-adipocyte differentiation and/or an action of anti-body weight gain, and at the same time the product does not have zapping bitterness as in the isomerized hop extract. Therefore, reports have been made that by blending the product with a food, the product can be directly ingested without taking a means of masking the bitterness, while expecting the physiological activities such as anti-adipocyte differentiation and anti-body weight gain (see, Patent Publications 2 and 3).

Patent Publication 4 discloses that a 2-acylfluoroglucinol-4,6-di-C-β-D-glucopyranoside, which is isolated from hops, has a strong antioxidant activity, so that the food blended with the compound is effective in diseases that interfere with the maintenance of health such as adult diseases and malignant rheumatoid arthritis.

Patent Publication 5 has reported that a fluoroacylphenone glycoside obtained by cold water extraction of a hop is expected to show an antioxidant action and an inhibitory action of tyrosinase activity, and that it is useful to contain the glycoside in the foodstuff.

On the other hand, Patent Publication 6 discloses a method for producing a hop extract containing xanthohumol in a high content, which has been known to have an anti-chemical carcinogenesis action or the like, in addition to antiviral action, anti-estrogen action, and anti-inflammatory action.

RELATED ART REFERENCES

Patent Publications

Patent Publication 1: Japanese Patent Laid-Open No. 2015-224194
Patent Publication 2: WO 2010/143719
Patent Publication 3: WO 2012/081675
Patent Publication 4: Japanese Patent Laid-Open No. 2008-174458
Patent Publication 5: Japanese Patent Laid-Open No. 2008-69072
Patent Publication 6: Japanese Patent Laid-Open No. 2015-134771

SUMMARY OF THE INVENTION

Problems to be Solved by the Invention

However, there are many functions not clarified for the hops.

An object of the present invention is to provide a hop processed product having an excellent action of anti-adipocyte differentiation and/or antioxidant action, a method for producing the hop processed product, and foodstuff in which the hop processed product is used as raw materials.

Means to Solve the Problems

Usually hop pellets are produced after collecting a large number of hops harvested at various harvest time points by hop producers in different farm fields in one produce area and blending the hops. Incidentally, from the view that the hops undergo hue changes according to the harvest time points, the present inventors have intensively studied remarking on the properties of the hops depending upon the hues. As a result, they have found that when pellets are prepared using hop flowers in a given amount or more showing a specified hue that have been harvested at an early stage, the pellets have excellent action of anti-adipocyte differentiation and antioxidant action, and the present invention has been perfected thereby.

The present invention relates to the followings [1] to [4]:

[1] A hop processed product for use in foodstuff for anti-adipocyte differentiation, containing 50% by weight or more of hop flowers (E•M) showing hues satisfying that a value of a* is less than −0.5 in accordance with a CIE Lab color space.

[2] A hop processed product for use in foodstuff for antioxidation, containing 50% by weight or more of hop flowers (E•M) showing hues satisfying that a value of a* is less than −0.5 in accordance with a CIE Lab color space.

[3] A method for producing a hop processed product as defined in the above [1] or [2], characterized by the use of hop flowers (E•M) showing hues satisfying that a value of a* is less than −0.5 in accordance with a CIE Lab color space, in an amount of 50% by weight or more of the hop flowers used as the raw materials.

[4] Foodstuff containing the hop processed product as defined in the above [1] or [2].

Effects of the Invention

Since the hop processed product of the present invention has an excellent action of anti-adipocyte differentiation and/or antioxidant action, the hop processed product can be suitably used as raw materials for foodstuff.

MODES FOR CARRYING OUT THE INVENTION

Figure 1:
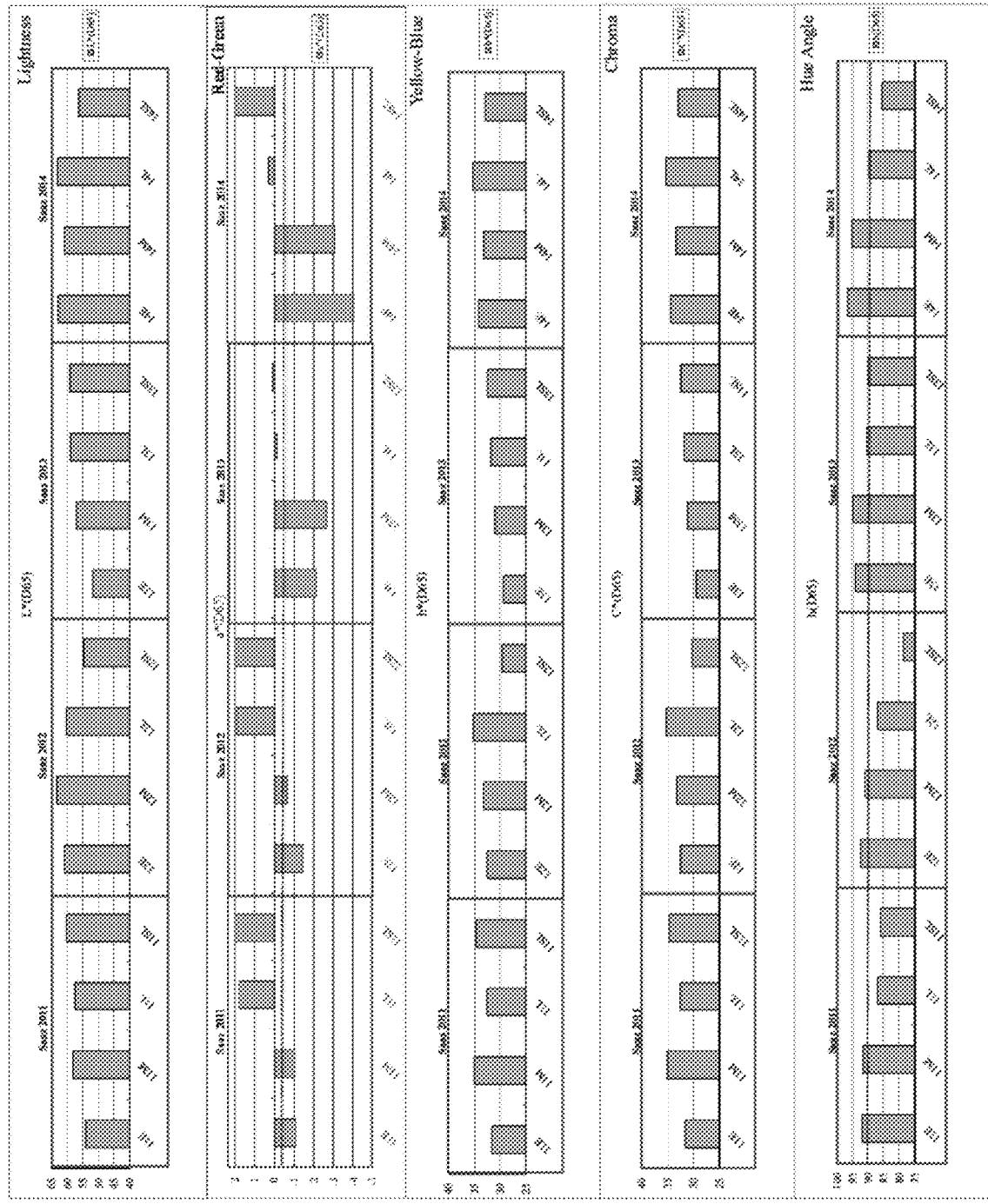
FIG. 1 is a set of graphs showing numerical values for each of coordinates in accordance with CIE Lab color space and CIE Lch color space for every harvest time points of hops.

The hop processed product of the present invention is characterized in that hop flowers (denoted as "hop flowers (E•M)"), showing hues satisfying that a value of a* is less than −0.5 in accordance with a CIE Lab color space, are used in an amount of 50% by weight or more as the raw materials. In the present specification, the hop flowers may be hereinafter simply referred to as "hops." Here, when the ranges are given by using "- (to)" as used herein, it is considered to include the numbers at both ends thereof.

In general, hops are started to be harvested from the day at which the amount of α-acids in the hops is at its maximum as a harvest initial date, and the harvest is ended usually in 25 days or so. In addition, the hops undergo yellowing in external appearance with the passage of time, so that the hop producers try front-loading the harvest timing, even within a usual harvest time point. For example, the hops are harvested within 15 days from the harvest initial date in many cases. On the other hand, the hops that have been harvested by front-loading the harvest timing are nearly the same in tones in the external appearance, so that it would be somewhat difficult to distinguish the hop processed products obtained by mixing them without discriminations. However, the present inventors have found that even with those hops obtained by front-loading the harvest timing, a hop processed product produced by selectively using a specified amount of a hop showing a particular tone has an excellent action of anti-adipocyte differentiation and/or antioxidant action. Meanwhile, conventionally, in the hops, polyphenol compounds such as xanthohumol, which is a prenylflavonoid, have been generally known as compounds having functional activities. Surprisingly, in the hops harvested at a certain early stage from the harvest initiation date, preferably within 15 days from the harvest initial date, the contents of the polyphenol compounds mentioned above are richly contained in the hop flowers (E•M) in which hues satisfying that a value of a* is a specified value in accordance with a CIE Lab color space are selected as an index, and the present inventors have surprisingly found for the first time that the above effects are strong. Here, the hues of the hop flowers as used herein refer to hues of hop flowers that are dried and powdered, which can be evaluated, for example, by a method described in Examples set forth below.

The hops which can be used in the present invention are not particularly limited in the areas of produce and varieties, and known aroma hops, bitter hops, and the like are used. Specific examples include aroma hops such as Hallertauer Mittelfrueh, Hallertauer Tradition, Hersbrucker, Perle, Tettnanger, Cascade, Saaz, and Sladek; and bitter hops such as Northern Brewer, Herkules, Magnum, Nugget, Taurus, Galaxy, and Target. In addition, as the parts thereof, the hops may be contained not only in lupulin portions, but also in bracts and leaves without any particular limitations.

The hop flowers (E•M) selected in the present invention have a value of a* in accordance with the CIE Lab color space of less than −0.5, and preferably −1 or less, and a hue leaning towards green is shown.

The hop flowers (E•M) used in the present invention have a value of a* in accordance with the CIE Lab color space as defined above, and have a value of b* in accordance with the CIE Lab color space of preferably a positive number of preferably less than 35, and more preferably 33 or less, and, and a hue too strongly leaning toward yellow is undesirable.

In addition, the hop flowers have a value of L* in accordance with the CIE Lab color space of usually a positive number; however, the numerical values fluctuate as the harvest time points fluctuate but certain tendencies could not be found. In any case, lightness is high. The hop flowers (E•M) used in the present invention have a value of L* of preferably 50 or more, more preferably 55 or more, and even more preferably 60 or more.

In addition, when the hop flowers are expressed by CIE Lch color space, which is different from the CIE Lab color space, a value of c* in accordance with the CIE Lch color space is usually a positive number; however, the numerical values fluctuate as the harvest time points fluctuate but certain tendencies could not be found. In any case, chroma is high. The hop flowers (E•M) used in the present invention have a value of c* of preferably 30 or more.

The value of h in accordance with the CIE Lch color space of the hop flowers is usually in a positive number, and the earlier the harvest time point, the higher the value. The hop flowers (E•M) used in the present invention have a value of h of preferably 90° or more, more preferably 94° or more, and even more preferably 95° or more.

The hop processed product of the present invention is not particularly limited in other raw materials, so long as the hop flowers (E•M) having hues as defined above are used as raw materials. Hop flowers having hues outside those hues as defined above may be used. The amount of the hop flowers (E•M) used having the hues as defined above in the entire raw materials is 50% by weight or more, preferably 60% by weight or more, and more preferably 70% by weight or more, from the viewpoint of more potently exhibiting the action of anti-adipocyte differentiation and/or the antioxidant action. The upper limit is not particularly limited, which may be 100% by weight.

The term "hop processed product" as used herein is not particularly limited in its form, and includes, for example, hop pellets, powder hops, hop extracts, and the like. Among them, hop pellets and hop extracts are preferred.

The hop processed product of the present invention is not limited in the method for production thereof, so long as the hop flowers (E•M) having hues as defined above are used in a specified amount as raw materials. Accordingly, one embodiment of the present invention includes a method for producing a hop processed product of the present invention, characterized by the use of hop flowers (E•M) showing hues satisfying that a value of a* is less than −0.5 in accordance with a CIE Lab color space, in an amount of 50% by weight or more of the hop flowers used as the raw materials.

Specifically, for example, in a case of producing hop pellets, raw materials containing 50% by weight or more of hop flowers (E•M) having hues as defined above may be furnished, and pelletized with a known tableting machine. Here, the hop pellets obtained have a value of a* in accordance with the CIE Lab color space of preferably less than −0.5, and more preferably −1 or less, and preferably −4 or more, and more preferably −3.5 or more. The hop pellets have a value of b* in accordance with the CIE Lab color space of preferably less than 35, and more preferably 33 or less, and preferably 25 or more, and more preferably 30 or more. In addition, the hop pellets have a value of h in accordance with the CIE Lch color space of preferably 90° or more, more preferably 94° or more, and even more preferably 95° or more, and preferably 100° or less, and more preferably 98° or less. In addition, the above values may fluctuate depending upon the amount of the hop flowers (E•M) used, and those within the above ranges are preferred.

In addition, in a case of producing a hop extract, raw materials containing 50% by weight or more of hop flowers (E•M) having hues as defined above can be furnished, and extracted with a known method. The extraction solvent, the temperature, the time, and the like can be appropriately set. Here, the extract obtained may be subjected to one or more treatments selected from the group consisting of filtration, centrifugation, concentration, ultrafiltration, lyophilization, powdering, and fractionation in accordance with a known method.

Thus, the hop processed product of the present invention can be obtained. The hop processed product of the present invention can be suitably used in foodstuff for action of anti-adipocyte differentiation, or foodstuff for antioxidant action, in order to exhibit the action of anti-adipocyte differentiation and the antioxidant action.

The term "action of anti-adipocyte differentiation" as used herein means an action of anti-adipocyte differentiation by inhibiting the process of differentiating adipocyte progenitor cells into adipocytes with a fat-inducing factor such as insulin. Specifically, the action can be evaluated in accordance with the method described in Examples set forth below.

The term "antioxidant action" as used herein means an action of antioxidation by scavenging active oxygen species in the body by taking a hop processed product of the present invention in the body. Specifically, the action can be evaluated in accordance with the method described in Examples set forth below.

The present invention also provides foodstuff containing a hop processed product of the present invention.

The foodstuff of the present invention may contain a hop processed product of the present invention in any forms, and include, for example, foodstuff for exhibition or improvements in actions of physiological activities for use in anti-adipocyte differentiation, antioxidation, and the like. Specifically, it is made possible to provide the foodstuff as foods for specified health use, foods with nutritional functional claims, foods for aged people, foods for special applications, functional foods, health supplements, with, for example, an indication such as "anti-metabolic syndrome," "anti-aging," or "anti-obesity," as an indication of the functions exhibited by anti-adipocyte differentiation, or the functions exhibited by antioxidation. The indication may be given to the foodstuff themselves, or may be given to the containers or wrappings of the foodstuff.

The foodstuff include, for example, luxury beverages such as carbonated drinks, fresh fruit juices, fruit juice beverages, refreshing beverages (including fruit juices), fruit pulp-containing beverages, fruit grains-containing fruit meat foods, vegetable-based beverages, soya milk and soya milk beverages, coffee beverages, green tea beverages, jelly beverages, powder beverages, concentrated beverages, sports beverages, and nutritious beverages; nutritious foods, supplements, pills, hard capsules, soft capsules, tablets (including raw tablets, dragees, orally fast disintegrating tablets, chewable tablets, foaming tablets, troches, film coating tablets, etc.); luxury beverages such as beer-taste beverages and luxury beverages; functional foods (foods for specified health use, foods with nutritional functional claims); animal feeds; pet foods; and the like. The amount used, the timing of addition, and the method of addition are not particularly limited so long as the hop processed product of the present invention is used as a raw material for the foodstuff. In addition, other components that are added and blended can be used without limitations, and the amounts used and the methods of addition can be appropriately selected in accordance with known techniques. The present invention encompasses those that are added after the preparation of the known foodstuff.

EXAMPLES

The present invention will be specifically described hereinbelow by the Examples, without intending to limit the scope of the present invention to the following Examples.

Test Example 1—Hues of Hop Flowers

As to the hop raw materials (variety: Saaz, area of produce: Czech Republic) produced in the years 2011, 2012, 2013, and 2014, the harvested hop raw materials were grouped in the order of the time points of harvest as follows: "Group E" is those hop raw materials harvested on the harvest initial date, "Group M" is those hop raw materials harvested 10 days from the harvest initial date, "Group L" is those hop raw materials harvested 25 days from the harvest initial date, and "Group SL" is those hop raw materials harvested 50 days from the harvest initial date. Hues were measured in accordance with the following conditions. Here, the harvest fiscal year and the harvest time points are expressed as a denotation of a combination of the last two digits of the harvested fiscal year together with the harvest time points to show the above groups. For example, "Group E" produced in 2013 would be denoted as "13E." In addition, as the pretreatment of the samples, the dry hop flowers of each of the groups were milled with a coffee mill, and the powdered product was directly used in the measurement. The measurement results are shown in Table 1 and FIG. 1.

<Measurement Conditions for Hues>
Color Space: CIE Lab color space
Measurement Instrument: Spectrocolorimeter CM-2002, manufactured by Minolta
Field Angle: 10° Field of View
Light Source: D65
Analyzing Software: SpectraMagic NX, manufactured by Minolta

TABLE 1

| Group Name | L*(D65) | a*(D65) | b*(D65) | c*(D65) | h(D65) |
|---|---|---|---|---|---|
| 11E | 54.17 | −1.09 | 31.62 | 31.64 | 91.97 |
| 11M | 58.19 | −1.04 | 34.99 | 35.00 | 91.70 |
| 11L | 57.59 | 1.77 | 32.56 | 32.61 | 86.89 |
| 11SL | 60.21 | 2.46 | 34.64 | 34.73 | 85.94 |
| 12E | 60.90 | −1.44 | 32.51 | 32.54 | 92.53 |
| 12M | 63.33 | −0.65 | 33.25 | 33.25 | 91.12 |
| 12L | 54.79 | 5.90 | 29.64 | 30.22 | 78.74 |
| 12SL | 54.91 | 6.50 | 29.91 | 30.61 | 77.74 |

TABLE 1-continued

| Group Name | L*(D65) | a*(D65) | b*(D65) | c*(D65) | h(D65) |
|---|---|---|---|---|---|
| 13E | 51.81 | −2.13 | 29.37 | 29.45 | 94.14 |
| 13M | 57.11 | −2.64 | 31.05 | 31.16 | 94.87 |
| 13L | 58.93 | −0.15 | 31.85 | 31.85 | 90.27 |
| 13SL | 59.14 | 0.08 | 32.45 | 32.45 | 89.86 |
| 14E | 62.95 | −4.01 | 34.19 | 34.42 | 96.69 |
| 14M | 60.89 | −3.05 | 33.23 | 33.37 | 95.25 |
| 14L | 63.06 | 0.29 | 35.32 | 35.32 | 89.54 |
| 14SL | 56.37 | 2.64 | 32.86 | 32.97 | 85.40 |

From Table 1 and FIG. 1, "Group 11E," "Group 11M," "Group 12E," "Group 12M," "Group 13E," "Group 13M," "Group 14E," and "Group 14M" had a value of a* in accordance with a CIE Lab color space of less than −0.5, which was greatly different from other groups of the same fiscal year. In addition, the values of h in accordance with a CIE Lch color space were from 91.12° to 96.69°, which were greatly different from those of "Group L" and "Group SL," respectively, in the comparisons within the same fiscal year. Accordingly, it can be seen that all of "Group 11E," "Group 11M," "Group 12E," "Group 12M," "Group 13E," "Group 13M," "Group 14E," and "Group 14M" are found to have numerical differences as compared to other groups, so that these groups are different in external appearance from those harvested in other time points.

Test Example 2—Polyphenol Components of Hop Flowers

Hop flowers that were grouped in the same manner as in Test Example 1 were pretreated in the same manner as in Test Example 1, and the pretreated samples were subjected to measurements in the contents of each of polyphenol components, the antioxidant activity, and the anti-adipocyte differentiation. Here, the denotations of the above grouped hops were the same as in Test Example 1, and in the measurements of the antioxidant activity and the anti-adipocyte differentiation, a commercially available reagent was purchased and measured in the same manner as a positive control. The measurement results are shown in Table 2 and FIGS. 2 to 4.

<Measurement Conditions for Contents of Each of Polyphenol Components>

Fifty grams of hop flowers were washed with 1 L of dichloromethane, and dichloromethane was then removed using folded filter paper. Thereafter, the hops were dried overnight under a draft. The dried hops were milled with a coffee mill. The amount 0.7 g of milled hops were added to 10 mL of a 70 v/v % acetone, and a mixture was stirred for 2 hours, and filtered with a filter paper. The hop residues on the filter paper were washed away twice with 10 mL of a 70 v/v % acetone, and received together with the filtrate. Using an evaporator, acetone was removed. Ten milliliters of MeOH and 20 mL of $H_2O$ were allowed to pass through Oasis HLB Plus to perform conditioning, and thereafter an extract was allowed to pass therethrough. After washing twice with 10 mL of $H_2O$, the washed product was extracted with 7 mL of MeOH (0.5 v/v % FA). The extract obtained was quantified in accordance with LC-MS to calculate the contents of polyphenol components per weight of the hops [column: Waters ACQUITY UPLC (registered trademark) BEH C18 (1.7 µm, 2.1×100 mm),
flow rate: 300 µL/min,
column temperature: 40° C.,
mobile phases: A) $H_2O$ (0.1 v/v % FA), B) MeCN (0.1 v/v % FA),
gradients: 0 minute (B solution: 2 v/v %)→30 minutes (B solution: 98 v/v %)→32 minutes (B solution: 98 v/v %)].

Here, the calibration curve was drawn by preparing Procyanidin standard solutions, using an extract obtained by processing with Oasis HLB Plus in the same manner as hop samples.

<Antioxidant Activity>

Each sample dissolved in DMSO was dissolved in a 50 v/v % EtOH, so as to prepare a sample solution having a concentration of 25, 50, and 100 µg/mL, and dispensed in each well of a 96-well plate in an amount of 100 µL each. Thereto was added 100 µL each of a DPPH solution dissolved in EtOH so as to have a concentration of 0.1 mM, and the mixture was stirred with vortex (final concentration: 12.5, 25, or 50 µg/mL). Next, the plate was made light-resistant with an aluminum foil, and allowed to stand at room temperature (25° C.) for 30 minutes, and the absorbance at 517 nm was then measured (n=3). Using the absorbance obtained, the DPPH radical scavenging rate (%) was calculated according to the following formula (1). Here, as for the blank, the absorbance was measured in the same manner as the sample solutions except that a 50 v/v % EtOH containing 0.2% DMSO was used.

$$DPPH \text{ Radical Scavenging Rate } (\%) = \frac{\text{Absorbance of Blank} - \text{Absorbance of Measurement Sample}}{\text{Absorbance of Blank}} \times 100$$

formula (1)

<Anti-Adipocyte Differentiation>
[Reagents]
Dulbecco's modified eagle medium (DMEM): 10% FBS (fetal bovine sera) and 1% penicillin/streptomycin were added thereto.
TrypLE™ Select (1×)
IBMX: prepared to have a concentration of 0.5 mM with DMSO.
DEX: prepared to have a concentration of 1 µM with DMSO.
insulin solution human
WST-8: upon use, diluted with the DMEM medium to give a 2% WST-8.
Oil Red O: prepared to have a concentration of 5 mg/mL with isoPrOH, and upon use, diluted with pure water to give a 60% Oil Red O.
[Method]
Day 1: 3T3-L1 Cells were previously cultured in a 10 cm dish to a state of 70 to 80% confluent. The 3T3-L1 cells were detached with TrypLE™ Select, and diluted with a DMEM medium to a concentration of 1.0×10⁵ cells/mL, 100 µL each of a cell suspension was then dispensed into a 96-well plate, and the cells were cultured at 37° C. under 5% $CO_2$.
Day 3: Each sample was prepared using a differentiation and induction medium (0.1% IBMX, 0.01% DEX). The medium of the cells that reached confluent was removed, and exchanged with 100 µL of a sample-containing differentiation and induction medium, and the cells were cultured at 37° C. for 2 days under 5% $CO_2$.
Day 5: Each sample was prepared using a differentiation medium (0.2% insulin). The differentiation and induction medium was removed, and exchanged with 100 μL of a differentiation medium, and the cells were then cultured for 3 days at 37° C. under 5% $CO_2$.

Day 8: Fifty microliters of the differentiation medium was removed and 100 μL of a fresh differentiation medium was added thereto, and the cells were cultured for 3 days at 37° C. under 5% $CO_2$.

Day 11: To a cultured medium was added 50 μL each of 2% WST-8, the cells were cultured for 3 days at 37° C. under 5% $CO_2$. One-hundred microliters of the medium was transferred to a fresh 96-well plate, and the absorbance at 450 nm was measured with a microplate reader. Using those cells, a cell viability (%) was calculated as a relative value to the control. The remaining medium was removed, formalin was then added thereto in an amount of 100 μL each, and the cell mixture was allowed to stand overnight at 4° C.

Day 12: Formalin was removed, 100 μL of a 60% iso-PrOH was then added thereto, and the cells were washed and then removed. Fifty microliters of a 60% Oil Red O reagent was added thereto, and a mixture was allowed to stand at room temperature for 10 minutes. The 60% Oil Red O reagent was removed, and each well was then washed with ultrapure water. The 96-well plate was dried, 50 μL of 100% isoPrOH was added thereto, a mixture was allowed to stand at room temperature for 10 minutes, and the absorbance at 520 nm was then measured. Using those cells, an adipocyte differentiation (%) was calculated as a relative value to the control.

Figure 2:
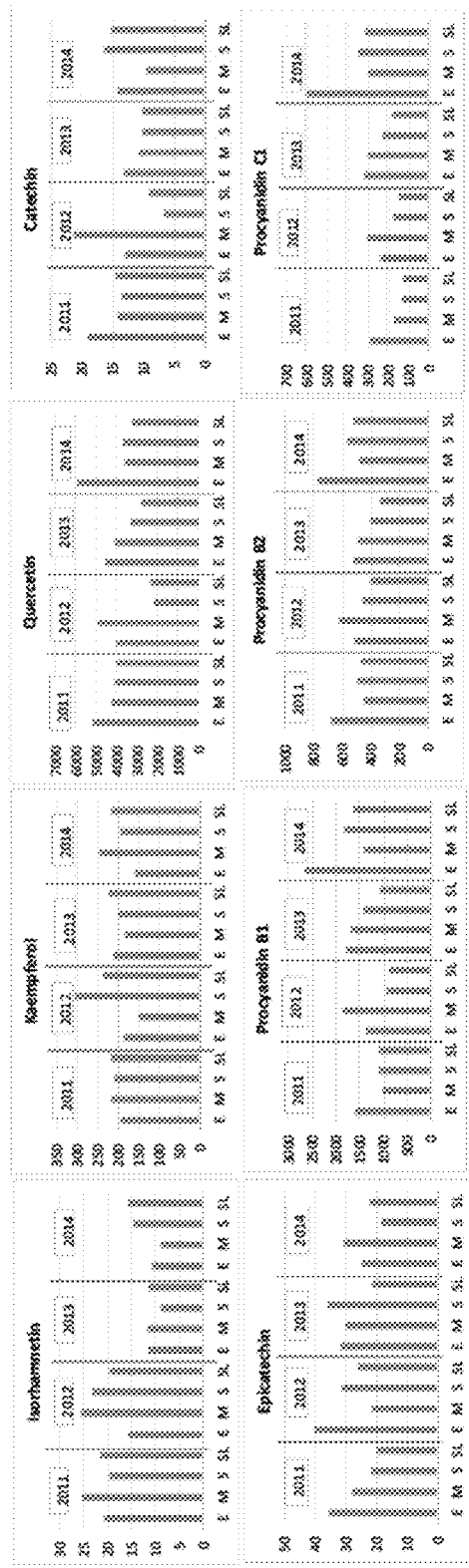
FIG. 2 is a set of graphs showing contents of the polyphenol components for every harvest time points of hops.

From Table 2 and FIG. 2, all of the polyphenol contents showed the same level or high contents in the comparisons within the same fiscal year in "Group 11E," "Group 11M," "Group 12E," "Group 12M," "Group 13E," "Group 13M," "Group 14E," and "Group 14M," as compared to those of each of "Group L" and "Group SL."

Figure 3:
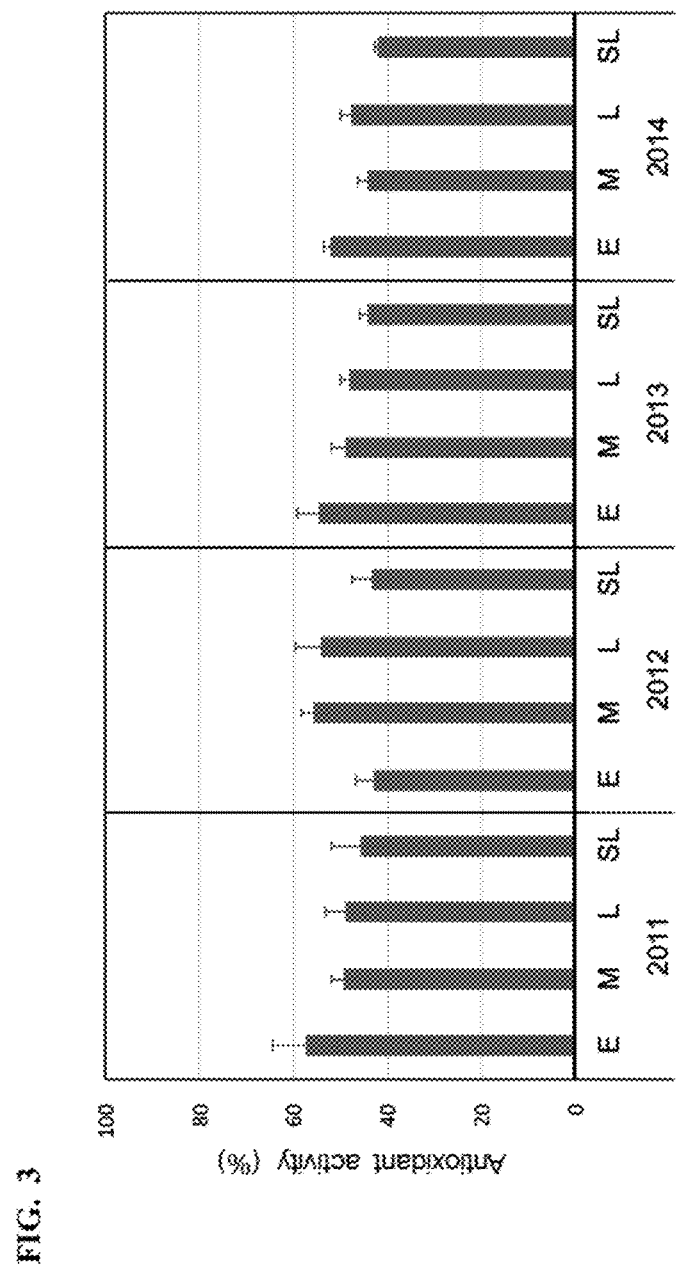
FIG. 3 is a graph showing an action for anti-adipocyte differentiation for every harvest time points of hops.
Figure 4:
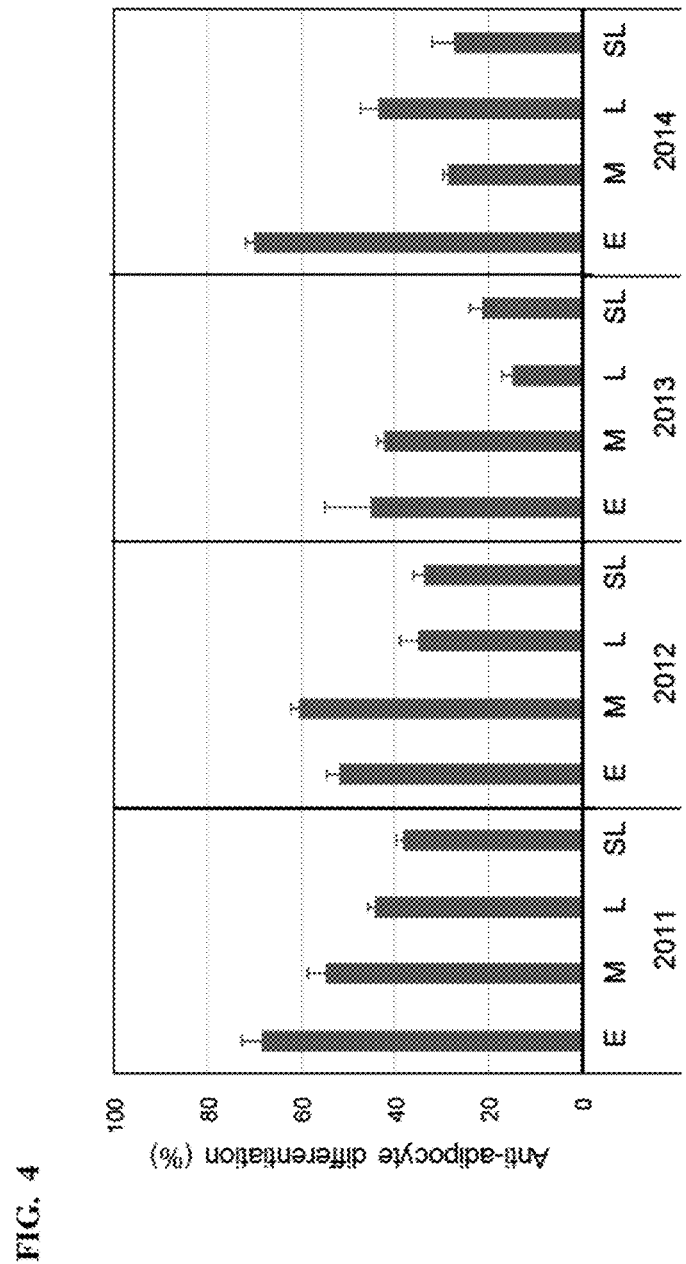
FIG. 4 is a graph showing an antioxidant action for every harvest time points of hops.

On the other hand, it could be seen from Table 2 and FIGS. 3 and 4 that the antioxidant effects and the anti-adipocyte differentiation effects were excellent in the comparisons within the same fiscal year in "Group 11E," "Group 11M," "Group 12E," "Group 12M," "Group 13E," "Group 13M," "Group 14E," and "Group 14M," as compared to those of each of "Group L" and "Group SL." Here, the antioxidant activity of a commercially available reagent "Vitamin C (12.5 μM)" was 70%, and the anti-adipocyte differentiation of "Quercetin (50 μM)" was 50%.

Specific formulations of foodstuff in which a hop processed product of the present invention is blended will be exemplified hereinbelow. These foodstuff can be prepared by known methods.

Raw materials such as at least one member selected from the group consisting of mugi such as malts, other grains, starches, and sugars, and optionally a bittering agent, a dye, or the like are supplied to a mashing kettle or tun, an enzyme such as amylase is optionally added to allow gelatinization or saccharification, thereafter husks or the like are removed by filtration to give a wort, the hop pellets which are a hop processed product of the present invention are then added to the wort obtained, and boiled, solid contents such as coagulated protein are removed in a clearing tank to give a clear

TABLE 2

| | Harvested Fiscal Year | | | | | | | |
| --- | --- | --- | --- | --- | --- | --- | --- | --- |
| | 2011 | | | | 2012 | | | |
| | Group Name | | | | | | | |
| | E | M | S | SL | E | M | S | SL |
| Isorhamnetin (mg/kg) | 20.8 | 25.3 | 19.5 | 21.6 | 15.7 | 25.6 | 23.2 | 19.5 |
| Kaempferol (mg/kg) | 192 | 216 | 208 | 215 | 184 | 148 | 304 | 236 |
| Quercetin (mg/kg) | 5187 | 4281 | 4108 | 4042 | 4049 | 4956 | 2228 | 2367 |
| Catechin (mg/kg) | 19.00 | 14.07 | 13.50 | 14.39 | 12.96 | 21.24 | 6.62 | 8.86 |
| Epicatechin (mg/kg) | 35.36 | 27.99 | 21.54 | 19.82 | 40.22 | 21.38 | 31.22 | 25.95 |
| Procyanidin B1(mg/kg) | 1597 | 1019 | 1095 | 1085 | 1373 | 1864 | 933 | 881 |
| Procyanidin B2(mg/kg) | 678 | 445 | 500 | 468 | 516 | 618 | 459 | 404 |
| Procyanidin C1(mg/kg) | 287 | 171 | 131 | 126 | 237 | 301 | 175 | 147 |
| Antioxidant Activity(%) | 57.5 | 49.3 | 48.8 | 45.8 | 42.8 | 55.6 | 54.0 | 43.3 |
| Anti-Adipocyte Differentiation (Cell Viability 100) (%) | 68.6 | 54.9 | 44.2 | 38.2 | 51.9 | 60.5 | 35.2 | 34.0 |

| | Harvested Fiscal Year | | | | | | | |
| --- | --- | --- | --- | --- | --- | --- | --- | --- |
| | 2013 | | | | 2014 | | | |
| | Group Name | | | | | | | |
| | E | M | S | SL | E | M | S | SL |
| Isorhamnetin (mg/kg) | 11.4 | 11.7 | 8.8 | 11.5 | 10.6 | 8.9 | 14.6 | 15.6 |
| Kaempferol (mg/kg) | 210 | 183 | 199 | 223 | 158 | 246 | 193 | 216 |
| Quercetin (mg/kg) | 4542 | 4112 | 3347 | 2815 | 5923 | 3603 | 3746 | 3277 |
| Catechin (mg/kg) | 13.11 | 10.56 | 10.08 | 10.15 | 14.09 | 9.39 | 16.27 | 15.11 |
| Epicatechin (mg/kg) | 31.62 | 30.03 | 35.77 | 21.28 | 24.81 | 30.56 | 18.59 | 22.20 |
| Procyanidin B1(mg/kg) | 1774 | 1677 | 1431 | 1071 | 2677 | 1399 | 1834 | 1622 |
| Procyanidin B2(mg/kg) | 518 | 490 | 401 | 334 | 774 | 483 | 563 | 521 |
| Procyanidin C1(mg/kg) | 317 | 297 | 227 | 180 | 599 | 298 | 349 | 314 |
| Antioxidant Activity(%) | 54.7 | 49.0 | 48.2 | 44.3 | 52.0 | 44.1 | 47.6 | 42.2 |
| Anti-Adipocyte Differentiation (Cell Viability 100) (%) | 44.9 | 42.3 | 14.8 | 21.3 | 70.0 | 28.7 | 43.7 | 27.5 | wort. As the conditions for these saccharification step, boiling-and-clarifying step, solid content-removing step, and the like, those of known ones may be used.

Next, in a case of an alcoholic beverage, the alcoholic beverage can be produced by adding an yeast to a clear wort obtained above to allow fermentation, and optionally removing the yeast with a filtration apparatus or the like. As the fermentation conditions, those of known ones may be used. Also, the hop flowers (E•M) in the present invention selected above after the beginning of fermentation or the hop pellets containing those hop flowers may be added. Alternatively, raw materials having an alcoholic ingredient such as spirits may be added in place of going through a fermentation step. Further, an alcoholic beer-taste beverage can be obtained by going through the steps of adding a stored liquor and optionally carbon dioxide gas, and subjecting to filtration and container filling, and optionally sterilization.

On the other hand, in a case of a nonalcoholic beverage, the nonalcoholic beverage is produced by going through the steps of, for example, subsequent to the above solid content-removing step, directly storing a clear wort obtained above, adding a carbon dioxide gas thereto, subjecting to filtration and container filling, and optionally sterilization. Alternatively, a nonalcoholic beer-taste beverage can also be obtained, subsequent to the fermentation step of the above alcoholic beverage, by reducing an alcohol concentration by a known method such as beer film treatment or dilution.

INDUSTRIAL APPLICABILITY

The hop processed product of the present invention has excellent action of anti-adipocyte differentiation or antioxidant action, so that the hop processed product can be expected to have effects in, for example, "anti-metabolic syndrome," "anti-aging," "anti-obesity," and the like.

The invention claimed is:

1. A method for producing a hop processed product, comprising:
    a providing step comprising providing harvested hop raw materials;
    an evaluating step comprising evaluating hues of hop flowers within the harvested hop raw materials with respect to a value of a* in accordance with a CIE Lab color space;
    a selecting step comprising selecting hop flowers (E•M) showing hues with a value of a* less than −0.5 in accordance with a CIE Lab color space wherein said hues are evaluated in the evaluating step to obtain a raw material hop flowers, wherein the raw material hop flowers comprise the hop flowers (E•M) in an amount of 50% or more by weight, based on the total weight of the hop flowers in the raw material hop flowers; and
    a processing step comprising processing the raw material hop flowers to obtain a hop processed, wherein the step of processing comprises processing the raw material hop flowers into a hop processed product selected from the group consisting of hop pellets, powder hops and hop extracts.

2. The method according to claim 1, wherein the hop processed product is in the form of hop pellets or hop extracts.

3. The method according to claim 2, wherein in case that the hop processed product is hop pellets, the value of a* of the hop pellets is less than −0.5 in accordance with a CIE Lab color space.

4. The method according to claim 2, wherein in case that the hop processed product is hop pellets, the value of a* of the hop pellets is within the range of from −1 or less to −4 or more in accordance with a CIE Lab color space.

5. The method according to claim 1, wherein the hop flowers (E•M) have the value of h of 90° or more.

6. The method according to claim 1, wherein said raw material hop flowers comprise hop flowers (E•M) in an amount of greater than 70% and less than 100% by weight, based on the total weight of the hop flowers in the raw material hop flowers.

7. A method of preparing a foodstuff exerting an anti-adipocyte differentiation action or an antioxidant action, comprising a step of adding and/or blending the hop processed product obtained in claim 1 to a foodstuff.

8. The method according to claim 7, wherein the foodstuff is selected from the group consisting of a beverage, nutritious food product, supplements, pills, hard capsules, soft capsules, tablets, animal feeds and pet food.

* * * * *